United States Patent [19]
Solomon et al.

[11] Patent Number: 5,417,116
[45] Date of Patent: May 23, 1995

[54] ACTIVE STRESS SPECIMEN USING AN ELECTROMAGNET AND BELLEVILLE WASHER

[75] Inventors: Harvey D. Solomon; Robert H. Ettinger, both of Schenectady, N.Y.

[73] Assignee: Electric Power Research Institute, Inc., Palo Alto, Calif.

[21] Appl. No.: 154,159

[22] Filed: Nov. 17, 1993

Related U.S. Application Data

[63] Continuation of Ser. No. 882,439, May 13, 1992, abandoned.

[51] Int. Cl.⁶ .................................................. G01N 19/00
[52] U.S. Cl. ........................................ 73/799; 73/810; 73/808
[58] Field of Search ............... 73/799, 810, 834, 835, 73/808, 786; 374/49, 50

[56] References Cited

U.S. PATENT DOCUMENTS

| | | | |
|---|---|---|---|
| 3,713,127 | 1/1973 | Keledy et al. | 340/267 |
| 3,908,447 | 9/1975 | Salt | 73/799 |
| 3,957,450 | 5/1976 | Salt . | |
| 3,983,745 | 10/1976 | Juusola | 73/799 |
| 4,075,884 | 2/1978 | Barker | 73/799 |
| 4,107,980 | 8/1978 | Crane et al. | 73/799 |
| 4,198,870 | 4/1980 | Barker et al. | 73/799 |
| 4,231,259 | 11/1980 | Thiruvengadam et al. | 73/584 |
| 4,266,185 | 5/1981 | Charlesworth et al. . | |
| 4,307,610 | 12/1981 | Leupp | 73/799 |
| 4,336,595 | 6/1982 | Adams et al. | 73/802 |
| 4,481,826 | 11/1984 | Ingraffea | 73/799 |
| 4,574,642 | 3/1986 | Fleischman | 73/799 |
| 4,665,984 | 5/1987 | Hayashi et al. | 73/784 |
| 4,756,194 | 7/1988 | Grandpierre et al. | 73/799 |
| 4,763,528 | 8/1988 | Bouami et al. | 73/799 |
| 4,801,641 | 1/1989 | Ogawa et al. . | |
| 4,814,301 | 3/1989 | Steinmann et al. . | |
| 4,836,029 | 6/1989 | Skala et al. | 73/799 |
| 4,924,708 | 5/1990 | Solomon et al. | 73/799 |

FOREIGN PATENT DOCUMENTS

| | | | |
|---|---|---|---|
| 2750461 | 5/1979 | Germany | 73/799 |
| 152933 | 8/1985 | Japan | 73/799 |
| 1610393 | 11/1990 | U.S.S.R. | 73/799 |

OTHER PUBLICATIONS

Hiroshi Tada, et al. The Stress Analysis of Cracks Handbook Jun. 1973, pp. 29.3; 29.4.

T. A. Prater et al, Smart Monitor/Smart Life Prediction Feasibility Study–I Aug. 1985, Section 2.

Juvinall, Robert C., Fundamentals of Machine Component Design 1983; pp. 384–386.

R. Pilkington, "Crack Opening displacement measurements at elevated temperatures", May 19, 1970, pp. 827–829.

Primary Examiner—Hezron E. Williams
Assistant Examiner—Nashimiya Ashraf
Attorney, Agent, or Firm—Flehr, Hohbach, Test, Albritton & Herbert

[57] ABSTRACT

An apparatus and method for inducing and measuring crack growth in a solid by using a double cantilever beam assembly which includes a fracture specimen with a notch that defines a pair of spaced outwardly extending beams terminating at an end where growth of a crack occurs, and a spring assembly for continuously urging the spaced beams apart with a substantially constant pressure that creates a spreading pressure at the end where crack growth occurs to stress the fracture specimen at the end. An electromagnet assembly is used to cyclically apply and remove the spreading pressure caused by the spring assembly.

13 Claims, 5 Drawing Sheets

SECTION A-A

FIG. 2B

SECTION B-B

ACTIVE STRESS SPECIMEN USING AN ELECTROMAGNET AND BELLEVILLE WASHER

This is a continuation of application Ser. No. 07/882,439, filed May 13,1992, now abandoned.

FIELD OF THE INVENTION

This invention relates generally to an improved apparatus and method for inducing and measuring the growth of a crack in a fracture specimen by two modes, either maintaining substantially uniform stress on the crack or cyclically applying and removing a substantially uniform stress from the crack.

BACKGROUND OF THE INVENTION

Exposing structural materials to aggressive environments under steady or cyclic stress can give rise to damage in the form of cracking. This is often referred to as "stress corrosion cracking" or "corrosion fatigue." Stress corrosion cracking of structural materials in aggressive environments is a continuing problem in many industries. The nuclear industry in particular continues to encounter this problem where the structural materials operate under sustained or cyclic stress in the presence of high temperature water.

Damage in the form of stress corrosion cracking, or other stress/environment-induced cracking, hereinafter referred to collectively as stress corrosion cracking, is of much greater concern in industry than damage such as that caused by uniform corrosion. Uniform corrosion results in a predictable service life for components. On the other hand material failures due to stress corrosion cracking are not easily predicted and are generally significant in nature.

U.S. Pat. No. 4,677,855 issued to Coffin, Jr. et al., the subject matter of which is hereby incorporated by reference, sets out problems which industry in general, and the nuclear industry in particular, faces in attempting to predict the onset of or susceptibility of particular structural components to stress corrosion cracking. In general, the performance of structural components is predicted in advance from information on the expected loadings and resulting stress from these loadings. Although these predictions are Sufficiently accurate to predict service performance, it is difficult to predict the lifetime of such performance due to uncertainty in the environmental conditions and the influence thereof on the stress corrosion cracking which results therefrom.

An example of the uncertainty of lifetime predictions for structural materials is the stress corrosion cracking which has been found to occur in stainless steel piping used in the nuclear industry. Although designs for new plants attempt to compensate for this phenomenon, it is desirable to monitor and assess the extent of damage in plants which have been operating for a number of years to help predict their lifetimes and possibly extend their lifetime. Methods for assessing the state of damage have been directed toward monitoring the aggressive environment. The water chemistry is measured to determine factors such as resistivity, electrochemical potential, oxygen level and impurity levels. Such measurements are indirect. No direct measurement is made of the effect this water chemistry has on crack growth in the structural materials during plant service. Therefore, the extent to which the lifetime of the structural material is extended by varying operating conditions are unknown.

Methods for directly measuring crack growth in specimens removed from their environment have been disclosed over the years, including a variety of monitoring systems using visual and voltage potential drop methods. An example of an apparatus for applying a spreading pressure to a slotted fracture specimen to induce cracking of the fracture specimen is disclosed by U.S. Pat. No. 4,075,884 issued to Barker. The Barker patent discloses applying a spreading pressure to the fracture specimen by inflating a pressure bag installed within the slot. Pressure for inflating the pressure bag is generated by a complicated specimen loading machine with a pressure chamber in which pressure is increases by the turning of a screw.

The apparatus disclosed in the Barker patent suffers from several disadvantages making it inoperable in the hostile environment of a nuclear reactor. First, the pressure bag may be adversely affected by the high temperatures, pressures and neutron flux in nuclear reactors. Second, the assembly for providing the pressure for the pressure bag is a complicated system involving a lot of equipment that is not useful in hostile environments and the limited space (approximately 18 inches) reserved for reactor surveillance specimens in a nuclear reactor. Due to the temperature, pressure, neutron flux, and space limitations, an electrical control system is more desirable and practical than a gas or fluid control system.

It was not until the method disclosed in the Coffin, Jr., et al. patent, that the industry was provided with the capability to accurately assess crack growth of plant structural components through voltage potential drop methods by disclosing a reasonably accurate way to relate voltage measurements to crack size. This method was improved upon by U.S. Pat. No. 4,924,708 issued to Solomon et al., the subject matter of which is hereby incorporated by reference.

Figure 1:
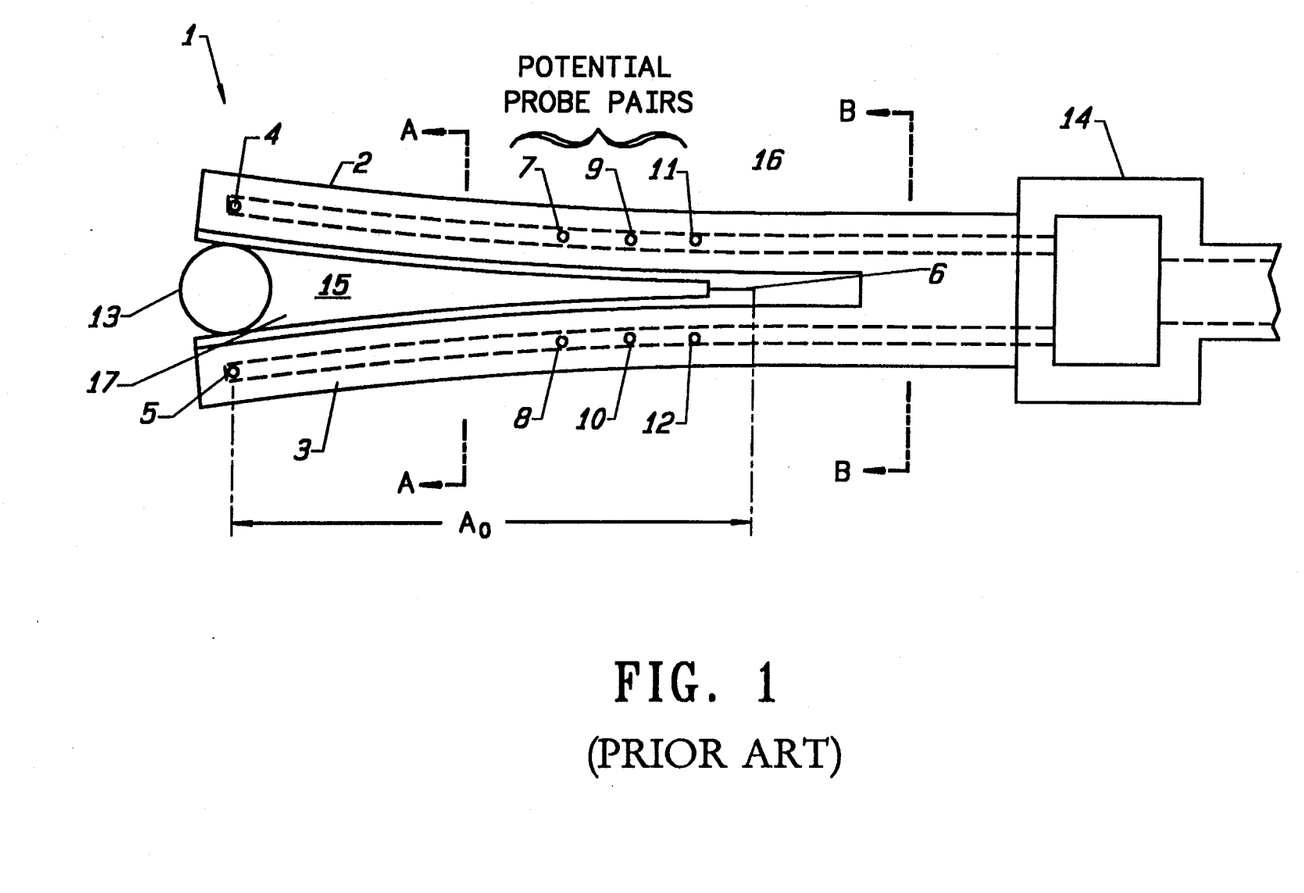
FIG. 1 is a side view of the conventional fracture specimen assembly.

The methods disclosed by the Coffin, Jr., et al. and Solomon et at. patents both utilize the same type of fracture specimen. Fracture specimen 1, disclosed by the Coffin, Jr., et at. and Solomon et al. and shown in FIG. 1, is of a double cantilever beam (hereinafter DCB) configuration. A voltage is applied to the ends of beams 2, 3 at points 4, 5, and the voltage drop across crack 6 is measured by pairs of probes 7, 8; 9, 10; 11, 12 positioned on each side of beams 2, 3. The changes in the voltage drop over time are used to calculate the growth of crack 6. When a current is caused to flow through fracture specimen 1 perpendicular to crack 6, the potential difference between two points located on opposite sides of the crack will increase as the size of crack 6 increases. Stress is placed on crack 6 by a spreading force acting to spread beams 2, 3 apart. The spreading force is created by stress creating member 13 that is positioned between beams 2, 3.

This DCB configuration suffers from two disadvantages. First, as crack 6 grows, the compliance of beams 2,3 increases. Since the size of stress creating member 13 is static, the stress placed on crack 6 by stress creating member 13 decreases as crack 6 grows. Second, the use of stress creating member 13 allows only for continuous stress on crack 6 as opposed to cyclical application and removal of the stress, i.e., fatigue stress, to more accurately reflect operating conditions.

This invention overcomes these disadvantages by applying a substantially constant stress to the crack and allowing for cyclical application and removal of stress to the crack. Moreover, the present invention is capable of operating in the hostile environment of a nuclear reactor.

SUMMARY OF THE INVENTION

It is a general object of the present invention to provide an improved apparatus and method for measuring crack growth in a fracture specimen.

It is another object of the present invention to provide an apparatus and method that applies a substantially constant stress to the crack in a fracture specimen.

It is also an object of the present invention to provide an apparatus and method that allows for cyclically applying and removing the stress from the crack in a fracture specimen.

It is a further object of the present invention to provide an apparatus and method that monitor the fracture specimen while the fracture specimen is in a hostile environment.

The foregoing and other objects of the invention are achieved by a double cantilever beam assembly which includes a fracture specimen with a notch that defines a pair of spaced outwardly extending beams terminating at an end where growth of a crack occurs, and a spring means for continuously urging the spaced beams apart with either a substantially constant pressure or cyclical pressure that creates a spreading pressure at the end where crack growth occurs to stress the fracture specimen at the end.

BRIEF DESCRIPTION OF THE DRAWINGS

The accompanying drawings, which are incorporated in and form a part of this specification, illustrate embodiments of the invention and, together with the description, serve to explain the principles of the invention.

DESCRIPTION OF THE PREFERRED EMBODIMENT

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the claims.

Turning now to the drawings, wherein like components are designated by like reference numerals, attention is initially directed to FIG. 1 where a conventional fracture specimen assembly for inducing the growth of crack 6 in fracture specimen 1 is shown. Fracture specimen 1 is made of a solid material of interest. Preferably, the material is electrically conductive, such as carbon or alloy steel, nickel and nickel based alloys, titanium and its alloys and nuclear structural materials such as austenitic stainless steels, ZrII, Inconel 600 TM and the like. This is necessary to obtain measurements of the electric potential across a crack in fracture specimen 1. It is preferable to manufacture fracture specimen 1 from the same material with the same process history as the structural components of interest. The size and shape of fracture specimen 1 can vary widely. Certain sizes and shapes may be preferred to enhance compactness, durability, sensitivity, simplicity of installment or flexibility.

Fracture specimen 1, shown in FIG. 1, has a double cantilever beam configuration, which has the virtue of being compact, self contained and allows for a considerable amount of crack growth. Beams 2, 3 extend outwardly from base 14 and are substantially parallel. Notch 15 is formed in the space between beams 2, 3. Crack 6, in which growth is measured, is formed in fracture specimen 1 at the closed end 16 of notch 15. Stress creating member 13 for applying spreading pressure to beams 2, 3 is positioned between beams 2, 3 near the open end 17 of notch 15. Electric potential probes 7, 9, 11 and 8, 10, 12 are placed on beams 2, 3, respectively, near the open end 17 of notch 15 for measuring voltage potential. Voltage is applied to fracture specimen 1 by electrical points 4, 5 positioned on the ends of beams 2, 3. Potential probe pairs are positioned on opposite sides of beams 2, 3 at fixed positions between the open 17 and closed 16 ends of notch 15 for measuring the voltage drop across crack 6. Methods for determining the growth in crack 6 from the measurements detected by the probe pairs are disclosed in the Coffin, Jr. et at. and Solomon et at. patents.

Figure 3:
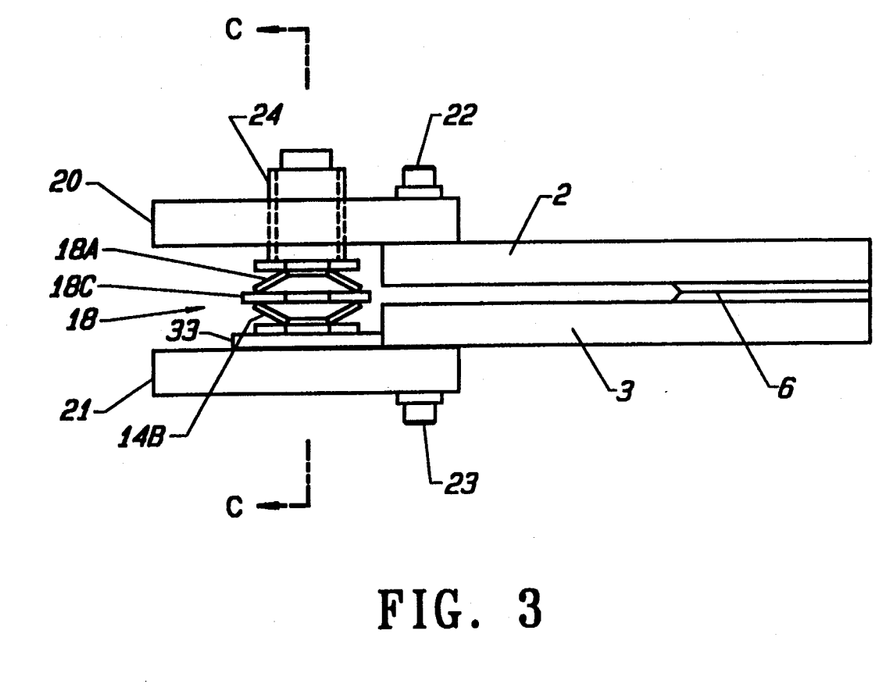
FIG. 3 is a side view of an embodiment of the present invention.
Figure 4:
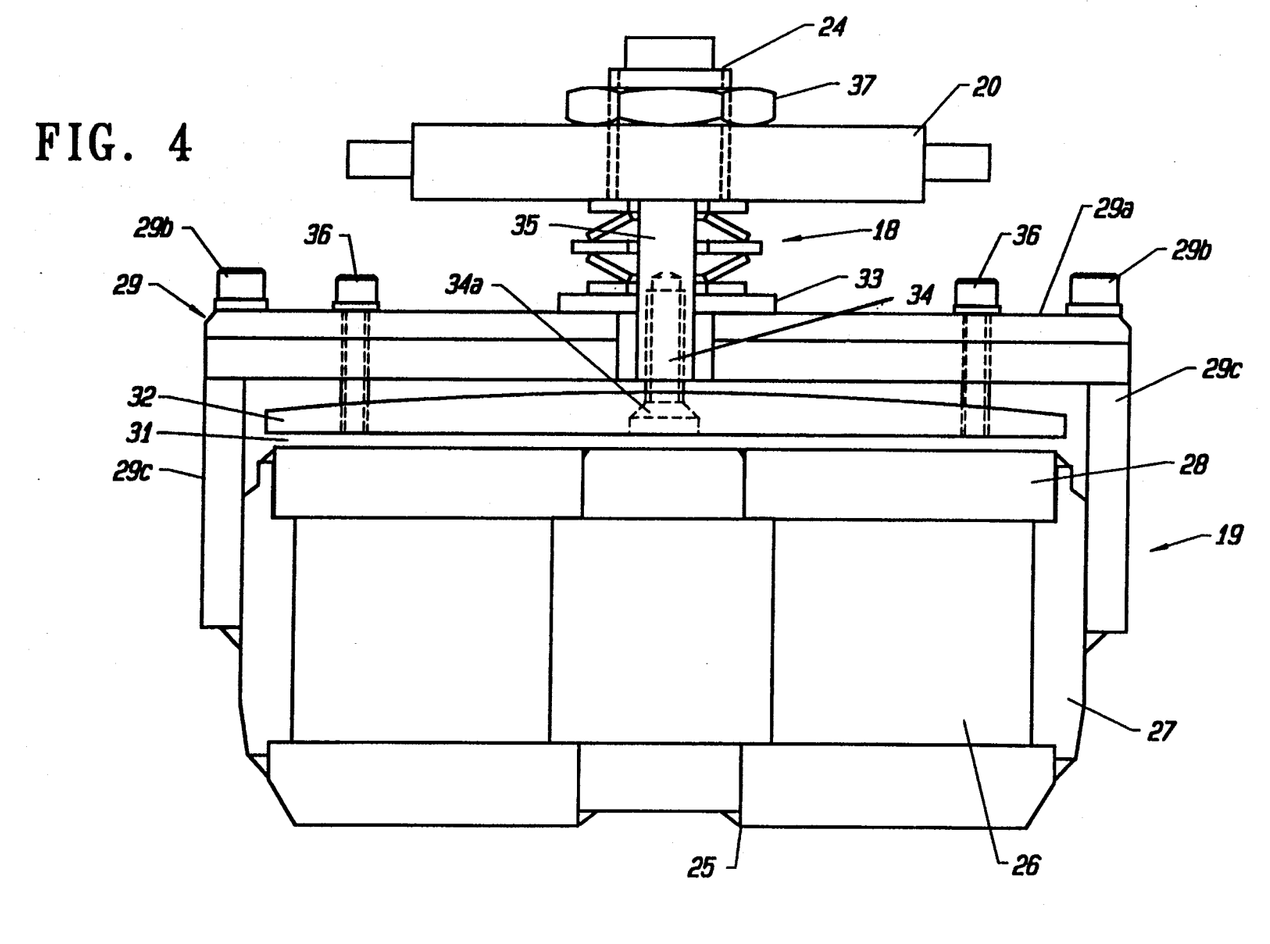
FIG. 4 is a sectional view of another embodiment of the present invention with an electromagnet, generally along axis C—C of FIG. 3.
Figure 5:
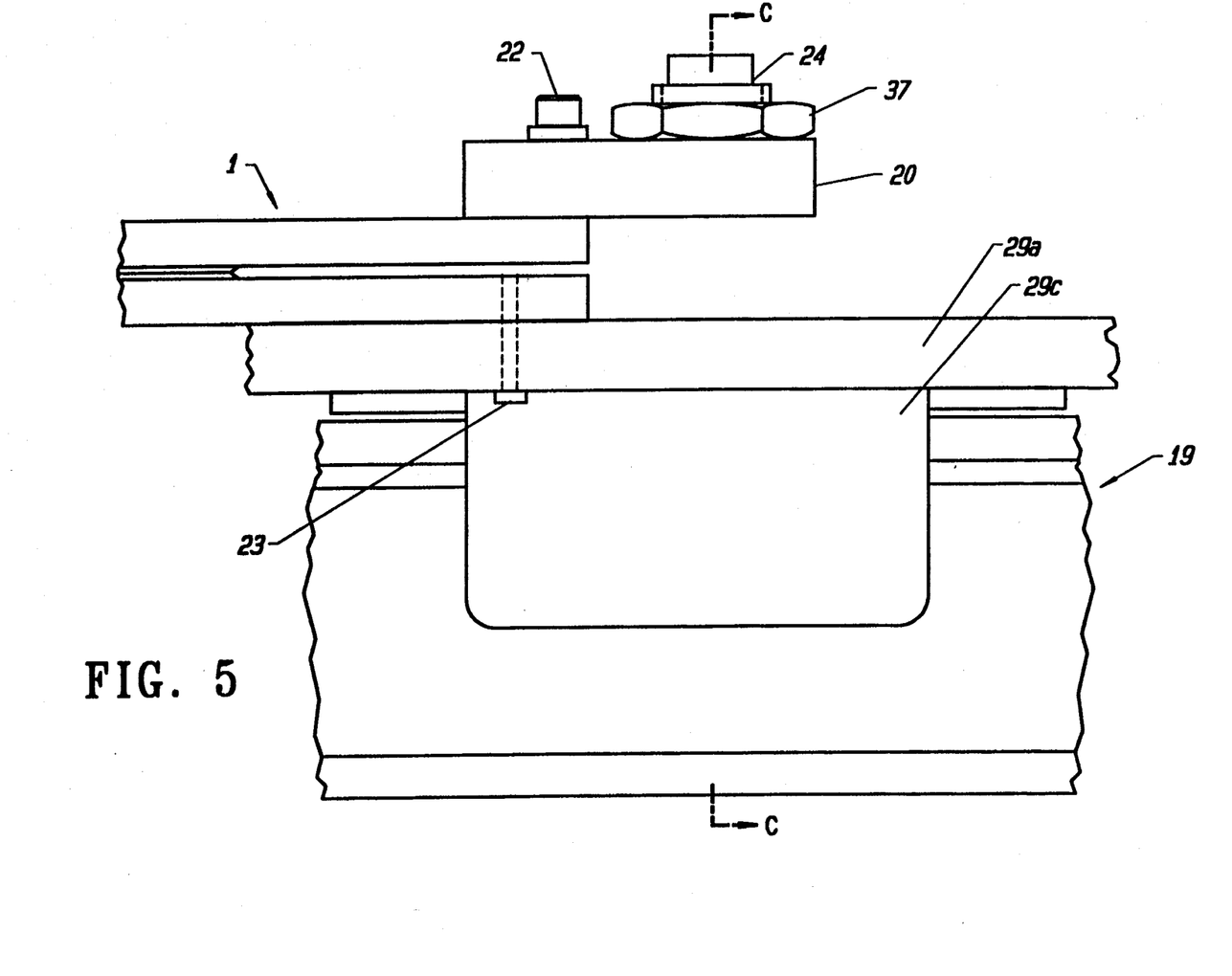
FIG. 5 is a side view of the present invention without the Belleville washer.

The present invention, shown in FIGS. 3–5, is an improvement over the fracture specimen assembly shown in FIG. 1. First, spring 18 (preferably Belleville washer(s)) are substituted for the stress creating member stressing the fracture specimen, as shown in FIG. 3. As crack 6 in fracture specimen 1 grows, the compliance of fracture specimen 1 also grows, and spring 18 will increase in length. This helps maintain a substantially constant stress intensity on crack 6.

The second feature is an electromagnet assembly 19 for compressing spring 18, which unstresses fracture specimen 1, as shown in FIG. 4. This active stressing and unstressing allows testing of fracture specimen 1 under a cyclical stress. Thus, the invention allows for testing under realistic operating conditions.

Fracture specimen assembly shown in FIG. 1, used for in-reactor tests, utilizes a ceramic stress creating member 13 to apply displacement D. Unfortunately, as crack 6 grows by stress corrosion cracking, the compliance of fracture specimen 1 increases and the stress applied by displacement D decreases.

In both cases, the compliance of the DCB increases with crack growth. The difference is that the compliance of the Belleville washers is much greater than that of the ceramic wedge. The washers can expand which reduces the amount of stress drop produced as the specimen compliance increase. The force P applied to fracture specimen 1 is represented by:

$$P = D/C \qquad (1)$$

where D is the displacement of beams 2, 3 and C is the compliance of fracture specimen 1. As fracture specimen 1 is stressed, D can increase as C increases, if Bellville washers are used to stress fracture specimen 1.

Thus, the decrease in P is small relative to when stress creating member 13, for which D is fixed, is used to stress fracture specimen 1.

Figures 2A, 2B:
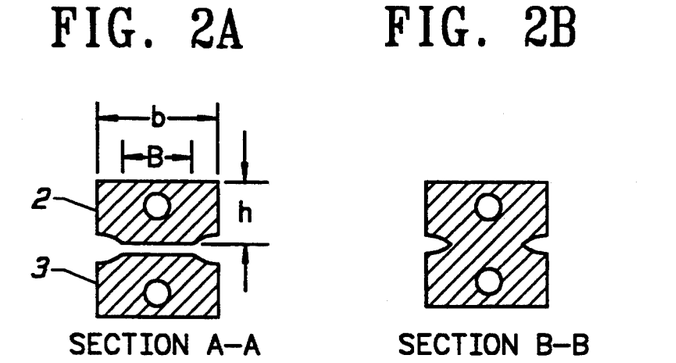
FIGS. 2A and 2B are front cross-sectional views of a fracture specimen along axes A—A and B—B, respectively, of FIG. 1.
Figure 2C:
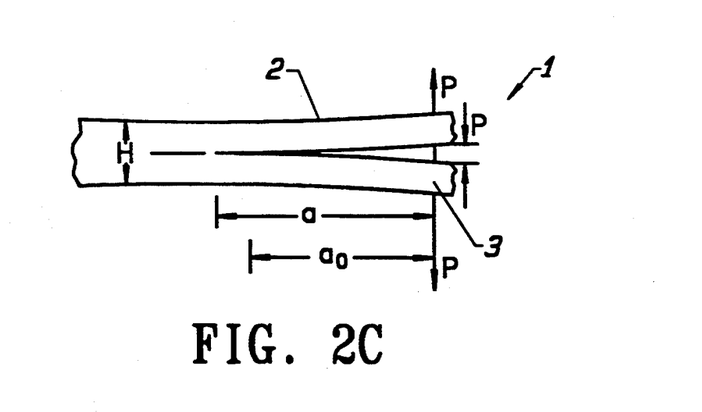
FIG. 2C is a side view of a fracture specimen.

The behavior of the stress intensity is readily apparent from the formulas 2 and 3 shown below. The variables relating to fracture specimen 1 are shown in FIGS. 2A–C. The general linear expression for stress intensity, K, is calculated in terms of either the force P or displacement D applied to the ends of beams 2, 3:

$$K = \frac{Pa}{\sqrt{2BI}} * \phi_1 * \phi_2 \qquad (2)$$

where $\phi_1 = 1$ for plane stress, and $$\frac{1}{\sqrt{1-\nu^2}} \text{ for plane strain}$$

$\nu$ = poisons ratio
$\phi_2$ = correction by cantilever bending at the crack tip and shear
E = elastic modules
I = movement of inertia
a = current crack length
B = inner ligament width of beams 2, 3.

Thus, if crack length a increases, displacement D and all other variables remain constant, the value of the stress intensity K will decrease.

The decay in the force applied to the ends of fracture specimen 1 is given by $P = D_{ceramic}/C$, where C is compliance and $D_{ceramic}$ is the fixed displacement with ceramic stress creating member 13. The compliance C is a function of the crack length and is given by:

$$C = \frac{a^3}{3EI} * \phi_3 \qquad (3)$$

$\phi_3$ = correction for cantilever bending at the crack tip and shear different from $\phi_2$.

From 2 and 3, one gets:

$$K = \frac{3ED}{a^2} \sqrt{\frac{I}{2B}} * \phi_1 * \frac{\phi_2}{\phi_3} \qquad (4)$$

The reduction in stress intensity is lessened by replacing ceramic stress creating member 13 with spring assembly 18, preferably Belleville washer(s). FIG. 3 shows fracture specimen 1 with spring assembly 18 consisting of two Belleville washers 18a, 18b and flat washer 18c. Flat washer 18c is positioned between Belleville washers 18a, 18b. Spring assembly 18 increases the displacement of fracture specimen 1 to compensate for increased compliance of fracture specimen 1.

The details of the invention utilizing Belleville washers for stressing fracture specimen 1 is described below. Fracture specimen 1 is a double cantilever beam configuration and is identical to the fracture specimen shown in FIG. 1 in all respects except for the means providing the stress and the means for cyclically stressing fracture specimen 1.

FIG. 3 shows the invention, excluding the cyclical stressing means. Spring assembly 18 is positioned between top plate 20 and bottom plate 21. Top plate 20 is fixed to top beam 2 by bolt 22, and bottom plate 21 is fixed to bottom beam 3 by bolt 23. Thus, when spring assembly 18 is compressed, force $P_{spring}$ is applied to top and bottom plates 12, 14, which spreads apart beams 2, 3. In order to compress spring assembly 18 to the desired length, compression screw 24 is inserted through top plate 20 and contacts the top of spring assembly 18. As compression screw 24 is tightened, spring assembly 18 is compressed.

Although the Figures only show a Belleville washer as spring assembly 18, any type of spring or similar means could be used to stress fracture specimen 1. Belleville washers are the preferred type of spring, since they are known in the art as useful for applying a large force over a short distance.

The benefits of substituting spring assembly 18 for stress creating member 13 are described below. As compliance of fracture specimen 1 increases, the compression of spring assembly 18 is reduced, i.e., length increases. This allows the displacement to increase, thereby substantially lessening the reduction in stress intensity, i.e., $P_{spring} = D_{spring}/C$ where spring assembly 18 washer expands to increase displacement $D_{spring}$ so that $D_{spring} > D_{ceramic}$, $P_{spring} > P_{ceramic}$. The force $P_{spring}$ applied by spring assembly 18 is substantially constant relative to the force $P_{ceramic}$ applied by stress creating member 13 (the force actually decreases in both cases but to a lessor degree with spring assembly 18). Thus, crack 6 experiences a lower stress intensity drop with spring assembly 18. A suitable choice of the spring constant for the Belleville washer enables the stress intensity to remain substantially constant.

The operation of the fracture specimen assembly with spring assembly 18, shown in FIG. 3, is described below. All equations and variables discussed below are applicable for spring assembly 18.

In operation, fracture specimen 1 is initially stressed by force $P_O = D_O/C_O$, where $D_O$ is the initial displacement and $C_O$ is the initial specimen compliance, by tightening compression screw 24. As compression screw 24 is tightened, beams 2,3 are monitored. Once the desired displacement is reached, tightening of compression screw 24 is stopped and fracture specimen 1 is ready for testing in the hostile environment. The initial displacement of spring assembly 18 is $D_{bO} = P_O C_b$ where $C_b$ is the spring compliance which is substantially constant.

As crack 6 grows from $a_O$ to $a_i$, fracture specimen 1 compliance increases to $C_i$. This causes fracture specimen displacement to increase by $\Delta_i$ from $D_o$ to $D_i$, and spring compression to correspondingly decrease by $\Delta_i$, where $\Delta_i = D_i - D_o$ (all movements are relative to the initial compressed condition) and $\Delta_i/C_b = P_O - P_i = -D_O/C_O - D_i/C_i$ (at $D_i$, force $P_i = D_i/C_i$, which is less than $P_O$). Rearranging the above equations yields:

$$\Delta_i = P_O * C_O ((1/C_O - 1/C_i))/(1/C_b + 1/C_i)) \qquad (5)$$

and $$P_i = P_O * ((C_O + C_b)/(C_i + C_b)) \qquad (6)$$

where $P_O$ is the initial force, $P_i$ is the current force applied by spring assembly 18. The current force $P_i$ is a function of the crack growth, which increases the specimen compliance. $P_i$ is used to calculate the stress intensity $K_i$ when fracture specimen 1 is stressed by spring assembly 18.

Unlike stress creating member 13 with fixed displacement D, the displacement of spring assembly 18 increases as the compliance of fracture specimen 1 increases. The stress intensity developed in fracture specimen 1 with spring assembly 18 is represented by:

$$K_i = K[(D_o + \Delta_i)/D_o] \quad (7)$$

where K is given by equation 4.

Beams 2,3 of fracture specimen 1 behave generally in a linear elastic manner; however, locally, at crack 6, non-linear mechanics dictate the behavior of fracture specimen 1. Although Eq. 7 is based on linear fracture mechanics, Eq. 7 is believed to be a suitable estimate of the stress intensity developed in fracture specimen 1.

With $C_b = 2.50 \times 10^{-4}$ in/lb, the increase in $\Delta_i$ compensates for the decrease in K (due to increased compliance) and keeps the stress intensity substantially constant for approximately 0.6" of crack growth. In contrast, for the same crack growth, the conventional fracture specimen assembly using ceramic stress creating member 13 experiences a drop in stress intensity of approximately 28% greater than experienced using Belleville washers 18a, 18b with a spring constant of $C_b = 2.5 \times 10^{-4}$. Thus, spring assembly 18 greatly reduces the drop in stress intensity which can accompany crack growth.

The stress on fracture specimen 1 is cycled by the state of electromagnet assembly 19. If electromagnet assembly 19 is de-energized, fracture specimen 1 is stressed by spring assembly 18. If electromagnet assembly 19 is energized, fracture specimen 1 is unstressed by believing the stress applied by spring assembly 18. The energization is accomplished by a power supply (not shown). Thus, de-energization and energization of electromagnet assembly 19 stresses and unstresses fracture specimen 1, respectively.

Active or cyclical stressing of fracture specimen 1 is accomplished by using flat face electromagnet assembly 19 in conjunction with spring assembly 18. FIG. 4 shows fracture specimen 1 with both spring assembly 18 and electromagnet assembly 19. Spring assembly 18 maintains a constant spreading force applied to beams 2, 3, electromagnet assembly 19 counteracts, when energized, the force of spring assembly 18 to unstress fracture specimen 1.

Electromagnet assembly 19 is formed by winding a coil around a 1¾ inch diameter low carbon steel mandrel 25. Twenty-six layers, with 27 turns per layer, of number 16 Hi-clad ™ Cu wire with S-glass insulating sleeving, is used to build up the magnet coil in region 26 of housing 27. During winding, germcast oxide potting compound (Aremco Products INC., Ossining, N.Y.) is filled in all space between windings. The winding is separated from the side retaining plates by mica glass. The coil is baked for 12 hours at 350° C. and then placed in carbon steel housing 27. Additional potting compound is added to completely cover the coil, then the assembly is re-baked. Mica glass insulates the coil from housing 27. Then, non-magnetic stainless steel face plate 28 is welded to the top of housing to completely seal electromagnet assembly 19 after the final bake out operation. The resulting overall electromagnet assembly 19 is approximately 6 inches in diameter and approximately 3 inches high. This process provides an electromagnet without organic binders or insulators, which can endure the hostile confines of a nuclear reactor.

Electromagnet assembly 19 is positioned below saddle 29 for pulling top plate 20 towards saddle 29 to compress spring assembly 18 and relieve the stress on fracture specimen 12. Saddle 29 is bolted, welded or otherwise mounted to the sides of electromagnet assembly 19 and is constructed either as a single piece or as a flat plate 29a fixed by screws 29b to side arms 29c that are welded to housing 27. Bottom beam 3 is connected to saddle 29 instead of bottom plate 21. Space 31 is left between saddle 29 and face plate 28 for attracting plate 32, which moves toward face plate 28 when electromagnet assembly 19 is energized and saddle 29 when electromagnet is de-energized.

An additional feature is insulator 33, which is positioned between spring assembly 18 and saddle 23. Insulator 33 does not effect the compression or expansion of spring assembly 18 but merely electrically insulates spring assembly 18 from electromagnet assembly 19.

In operation, electromagnet assembly 19 is normally de-energized which stresses fracture specimen 1. The spring assembly 18 is free to stress fracture specimen 1, since electromagnet does not apply an opposing force to spring assembly 18 when de-energized. Energizing electromagnet assembly 19 pulls fracture specimen beams 2, 3 together, compressing spring assembly 18 and removing all or pan of the spreading force from fracture specimen 1. In order to overcome the force of spring assembly 18, the attracting force of energized electromagnet assembly 19 must be greater than the force of spring assembly 18 when fully compressed. When electromagnet assembly 19 is de-energized, the force of spring assembly 18 re-stresses fracture specimen 1.

Electromagnet assembly 19 pulls beams 2, 3 together by the force acting on attracting plate 32. As shown in FIG. 4, attracting plate 32 is rotatably fixed by tilting pin 34 to connecting rod 35, which is an extension of compression screw 24. Connecting rod 35 passes through holes in the center of spring assembly 18, insulator 33 and saddle 29. The diameter of connecting rod 35 is smaller than the diameter of the holes in spring assembly 18, insulator 33 and saddle 29 to allow connecting rod 35 to move unhindered within the holes. The space is necessary since connecting rod 35 moves at a slight angle rather than truly vertically due to the motion of top beam 2 during expansion and compression of spring assembly 18.

The shape of the top of attracting plate 32 and tilting pin 34 allow for attracting plate 32 to tilt universally. The tilting is to provide the best possible attraction between attracting plate 32 and electromagnet assembly 19, and to prevent the top edge of attracting plate 32 from contacting saddle 29 before spring assembly 18 is expanded or compressed, respectively. These potential problems are created by the motion of to beam 2 during expansion and compression of spring assembly 18, which moves connecting rod 35 up and down at a slight angle off the vertical. Thus, if attracting plate 32 is rigidly fixed to connection rod 35, attracting plate 32 will not lie substantially parallel to electromagnet assembly 19 while attracting plate 32 is pulled toward energized electromagnet assembly 19.

The hole in attracting plate 32, through which tilting pin 34 is inserted, is machined to match the rounded shape of the head 34a of tilting pin 34. This allows tilting of attracting plate 32 in the plane parallel to tilting pin 30. Moreover, the top of attracting plate 32, which faces saddle 29, is bevelled to help prevent the top of attracting plate 32 from hitting saddle 29 when the attracting plate is tilted to become parallel to the face of the magnet. Additionally, set screws 36 may be inserted through saddle 29 to limit the tilting of attracting plate 32.

Since the action of attracting plate 32 pulls top plate 20 via compression screw 24, lock nut 37 is placed on top plate 20 around compression screw 24. This locks screw 24 to prevent unwanted rotation.

When electromagnet assembly 19 is de-energized and spring assembly 18 spreads apart beams 2, 3, connecting rod 35 is sufficiently long so that attracting plate 32 does not contact saddle 29. Clearance between attracting plate 32 and flat plate 29a of saddle 29 is required so that attracting plate 32 does not interfere with the increasing displacement of beams 2, 3 as the compliance of fracture specimen 1 increases with crack growth. The amount of clearance between attracting plate 32 and flat plate 29a is controlled by the length of connecting rod 35 and the clearance between flat plate 29a and electromagnet assembly 19. Moreover, the clearance and the length of connecting rod 35 can be adjusted so that when electromagnet assembly 19 is energized, beams 2, 3 do not completely return to their original unstressed position. Thus, when electromagnet assembly 19 is energized, a reduced stress is applied to fracture specimen 1.

A prototype sealed housing was tested at 288° C. and 1500 PSI pressure to insure that it would not distort. Additionally, electromagnet assembly 19 was hydro tested at 288° C., 1500 PSI to check for potential leakage. Tests indicate the invention is effective at high temperature and pressure without the use of organic binders or insulators. Standard binders and insulators are generally made of organic materials. Although organic materials are effective at 288° C., neutron flux turns organic materials to powder. Thus, the prototype electromagnet was designed without organic binders and insulators so that the prototype could operate effectively in a high neutron flux environment.

While the present invention has been shown and described in what is presently conceived to be the most practical and preferred embodiment of the present invention, it will become apparent to those of ordinary skill in the art that many modifications thereof may be within the scope of the invention, which scope is to be accorded the broadest interpretation of the claims so as to encompass all equivalent structures and devices.

What is claimed:

1. A double cantilever beam assembly comprising:
   a fracture specimen having a notch which defines first and second spaced, substantially parallel, outwardly extending beams terminating at a closed end where crack growth occurs and extending to an open end;
   a first plate fixedly mounted to said first beam and extending outwardly from said first beam in a direction substantially parallel to said first beam;
   a second plate spaced from said first plate fixedly mounted to said second beam and extending outwardly from said second beam in a direction substantially parallel to said second beam;
   said first plate and said second plate providing an extension of said first and second beams, respectively, with said notch opening into the space between said first plate and said second plate;
   a spring at a position in said space between said first and second plates for continuously urging said first and second plates apart with a substantially constant pressure whereby to create spreading pressure at said closed end to stress said fracture specimen at said closed end.

2. The double cantilever beam assembly as recited in claim 1, further comprising:
   an unloading means for selectively urging said spaced beams together.

3. The double cantilever beam assembly as recited in claim 2, wherein said unloading means is an electromagnet.

4. The double cantilever beam assembly as recited in claim 1, further comprising:
   sensor means positioned along said spaced beams across said crack for measuring a voltage drop across said crack when a voltage is applied to said fracture specimen.

5. The double cantilever beam assembly as recited in claim 1, further comprising:
   electromagnetic means for engaging and urging said first and second beams together, in opposition to said continuously urging by said spring, when said electromagnetic means is energized.

6. The double cantilever beam assembly as recited in claim 5, further comprising:
   an attracting means in communication with said first beam, wherein said electromagnetic means attracts said attracting means when energized, which pulls said first beam towards said second beam.

7. A double cantilever beam assembly comprising:
   a fracture specimen having a notch extending inwardly from a front surface of said specimen and terminating at a closed end where crack growth occurs, said notch defining a pair of spaced beams;
   upper and lower plates each mounted to one of said spaced beams, said upper and lower plates extending outwardly from said front surface of said specimen in a direction parallel to said spaced beams and each of said plates having an outer edge spaced from said front surface of said specimen, said upper and lower plates defining a channel extending inwardly from said outer edges of said upper and lower plates to an open end of said notch;
   a loading means for cyclically applying pressure to and removing pressure from said beams for cyclically urging said spaced beams apart, wherein said applying of pressure causes spreading at said closed end to stress said fracture specimen and said removing of pressure prevents spreading at said closed end to unstress said fracture specimen;
   said loading means having a spring positioned in said channel between said upper and lower plated for continuously urging said upper and lower plates and said spaced beams apart and a stress removing means for selectively urging said spaced beams together in response to an unstress signal.

8. A double cantilever beam assembly comprising:
   fracture specimen having a notch which defines a pair of spaced outwardly extending beams terminating at an end where crack growth occurs; and
   a spring for continuously urging said spaced beams apart with substantially constant pressure whereby to create spreading pressure at said end to stress said fracture specimen at said end, said spring including at least one Belleville washer.

9. A double cantilever beam assembly comprising:
   a fracture specimen having a notch which defines first and second spaced, substantially parallel, outwardly extending beams terminating at a closed end where crack growth occurs and extending to an open end;

a first plate fixedly mounted to said first beam and substantially parallel to said first beam;

a second plate fixedly mounted to said second beam and substantially parallel to said second beam;

a spring at a position between said first and second plates for continuously urging said first and second plates apart with a substantially constant pressure whereby to create spreading pressure at said closed end to stress said fracture specimen at said closed end;

electromagnetic means for engaging and urging said first and second beams together, in opposition to said continuous urging by said spring, when said electromagnetic means is energized;

an attracting means in communication with said first beam, wherein said electromagnetic means attracts said attracting means when energized, which pulls said first beam toward said second beam, said attracting means being rotatably fixed to said first plate, such that said attracting means can tilt to prevent said attracting means from interfering with the urging of said beams apart and together.

10. A method for measuring crack growth in a fracture specimen having a notch which defines a pair of spaced outwardly extending beams having an open end and terminating at a closed end where crack growth occurs, comprising the steps of:

mounting upper and lower plates to said spaced beams with said upper and lower plates extending from said open end of said spaced beams in a direction substantially parallel to said spaced beams and said upper and lower plates extending to define a channel therebetween terminating at said open end of said notch;

positioning a spring in said channel between said upper and lower plates;

continuously engaging and urging said spaced beams apart with said spring applying substantially constant pressure to said upper and lower plates whereby to create spreading pressure at said closed end to stress said fracture specimen at said closed end;

detecting growth of said crack at said closed end created by said continuously urging of said spaced beams.

11. The method recited in claim 10, wherein said step of detecting comprises:

applying a current to said spaced beams to produce a potential field within said fracture specimen whereby a voltage drop is created across said crack; and sampling said voltage drop at positions along said spaced beams to determine growth in said crack.

12. The method recited in claims 10, further comprising the step of:

cyclically urging said spaced beams together to remove said spreading pressure at said end created by said continuously engaging and urging step to stress and unstress said fracture specimen.

13. A method for inducing crack growth in a fracture specimen having a notch which defines a pair of spaced outwardly extending beams having an open end and terminating at a closed end where crack growth occurs, comprising the steps of:

mounting upper and lower plates to said spaced beams with said upper and lower plates extending from said open end of said spaced beams in a direction substantially parallel to said spaced beams and said upper and lower plates extending to define a channel therebetween terminating at said open end of said notch;

positioning a spring in said channel between said upper and lower plates;

continuously engaging and urging said spaced beams apart with a spring applying substantially constant pressure to said upper and lower plates whereby to create spreading pressure at said closed end to stress said fracture specimen at said closed end; and cyclically urging said spaced beams together to remove said spreading pressure at said closed end created by said continuously; engaging and urging step to unstress said fracture specimen.

* * * * *